United States Patent
Leach et al.

(10) Patent No.: US 6,596,707 B2
(45) Date of Patent: Jul. 22, 2003

(54) MONOVALENT SACCHARIDES AND USES THEREOF

(75) Inventors: James L. Leach, Columbus, OH (US); Stacey A. Garber, Dublin, OH (US); Pedro A. Prieto, Columbus, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/864,999

(22) Filed: May 24, 2001

(65) Prior Publication Data

US 2003/0040503 A1 Feb. 27, 2003

(51) Int. Cl.[7] .................. A01N 43/04; A61K 31/715
(52) U.S. Cl. .................. 514/61; 514/54; 514/62; 536/18.7; 536/22.1; 536/55; 536/55.1; 536/55.2; 536/123.1
(58) Field of Search ............. 536/18.7, 22.1, 536/55, 55.1, 55.2, 123.1; 514/54, 61, 62

(56) References Cited

U.S. PATENT DOCUMENTS

| | | | | |
|---|---|---|---|---|
| 4,923,980 A | * | 5/1990 | Blomberg | 536/55.3 |
| 5,288,637 A | | 2/1994 | Roth | |
| 5,474,986 A | * | 12/1995 | Magnusson et al. | 514/53 |
| 5,484,773 A | * | 1/1996 | Heerze et al. | 514/23 |
| 5,846,943 A | * | 12/1998 | Hindsgaul et al. | 514/25 |
| 5,888,750 A | * | 3/1999 | Vanmaele et al. | 435/7.8 |
| 5,922,848 A | * | 7/1999 | Vanmaele et al. | 530/413 |
| 5,945,314 A | | 8/1999 | Prieto et al. | |
| 6,121,242 A | | 9/2000 | Rafter et al. | |

OTHER PUBLICATIONS

Karen L. Kotloff, M.D., *Bacterial Diarrheal Pathogens, Advances in Pediatric Infectious Diseases*, vol. 14, Mosby, Inc. (1999).

Merritt E.A. & Hol, Wim G.J., $AB_5$ toxins, *Current Opinion in Structural Biology*, 5: 165–171, (1995).

Boyce, TG, et al., *Escherichia Coli* O157:H7 and The Hemolytic–Uremic Syndrome, *The New England Journal of Medicine*, 333(6): 364–368, (1995).

Donnelly, John J., et al., Blocking Bacterial Enterotoxins, *Natural Medicine*, 6(3): 257–258, (2000).

Kitove, P.I., et al., Shiga–like Toxins are Neutralized by Tailored Multivalent Carbohydrate Ligands, *Nature*, 403:669–672, (2000).

Armstrong, Glen D., et al., A Phase I Study of Chemically Synthesized Verotoxin (*Shiga–like Toxin*) Pk–Trisaccharide Receptors Attached to Chromosorb for Preventing Hemolytic Uremia Syndrome, *The Journal of Infectious Desease*, 171:1042–5, (1995).

Walker, W.A., et al., Role of Oligosaccharides and Glycoconjugates in Intestianal Host Defense, *JPGN*, Mar., 2000.

* cited by examiner

Primary Examiner—James O. Wilson
Assistant Examiner—Patrick Lewis
(74) Attorney, Agent, or Firm—Cheryl L. Becker (57) ABSTRACT

The subject invention relates to monovalent oligosaccharides and their use, for example, in the treatment and prevention of mammalian disease caused by infection with Shiga toxin (ST) or Shiga-like toxin (SHL). In particular, the trisaccharide globotriose (i.e., galactose α1,4 galactose β1,4 glucose) may be used to competitively inhibit binding of the toxins to their cellular targets.

4 Claims, 3 Drawing Sheets

HPLC CHROMATOGRAM OF SYNTHESIZED GLOBOTRIOSE (KYOWA) COMPARED TO STANDARD GLOBOTRIOSE FROM SIGMA AND V-LABS.

FIG.3

MONOVALENT SACCHARIDES AND USES THEREOF

BACKGROUND OF THE INVENTION

1. Technical Field

The subject invention relates to monovalent oligosaccharides and their use, for example, in the treatment and prevention of mammalian disease caused by Shiga toxin (ST) and Shiga-like toxin (S-LT). In particular, the trisaccharide globotriose (i.e., galactose α1,4 galactose β1,4 glucose) may be used to effectively prevent the pathological binding of ST and S-LT to target cells bearing the globotriaosylceramide glycolipid and to reverse this pathological binding once it has occurred.

2. Background Information

Shigellae are gram-negative, non-lactose-fermenting, non-motile bacilli of the family Enterobacteriaceae and are classified into four species. Shigella bacteria invade and kill intestinal epithelial cells causing colonic inflammation, muscosal ulceration and hemorrhage. Shiga Toxin (ST) is produced by *Shigella dysenteria*, the pathogen that causes dysentery. Secreted ST irreversibly inhibits protein synthesis by ADP-ribosylation of a key moiety of the ribosome. ST is cytotoxic for a variety of cell types, important among which are intestinal enterocytes, vascular endothelium and neurons.

Similar disease and cellular damage are caused by one distinct category of *Escherichia coli* which is present worldwide as a result of contaminated food or water. *E. coli* are gram-negative, lactose-fermenting motile bacilli of the family Enterobacteriaceae. Specifically, enterohemorrhagic *E. coli* (EHEC) produce a family of cytotoxins, termed Shiga-like toxins (S-LTs), which are closely related to those produced by Shigella. EHEC adhere to colonic enterocytes causing mucosal ulceration. Secretion of S-LT is essential to the pathogenesis of disease and results in hemorrhagic necrosis of affected tissue. As with ST, S-LTs can cross the intestinal mucosa to the circulation and bind to a variety of cells causing additional pathology. (Karen L. Kotloff, "Bacterial Diarrheal Pathogens". *Advances in Pediatric Infectious Diseases,* vol. 14 Mosby, Inc. 1999)

ST and S-LT are two members of a general class of bacterial $AB_5$ toxins, which cause a spectrum of pathology in humans and animals. The $AB_5$ toxins are characterized by a catalytic A subunit and a pentamer of B subunits that bind to specific glycolipids embedded in the exterior portion of the lipid bi-layer of animal cells. The binding of the B pentamer induces internalization of the holotoxin where the catalytic A subunit causes cytoxic damage. The animal and tissue tropism exhibited by the $AB_5$ toxins is mediated by the binding specificity of the B subunit for particular oligosaccharide structures found on distinct glycolipids.

It is well accepted that the recognition motif for both ST and S-LT is the oligosaccharide portion of the globoseries-glycolipid globotriaosylceramide found on the exterior of a wide variety of mammalian cells. The free oligosaccharide (Galα1,4Galα1,4Glc) portion of globotriaosylceramide is known as globotriose. (Merritt E A & Hol W G J. $AB_5$ toxins. Current opinion in structural biology 1995, 5:165–171).

The spectrum of clinical manifestations of gastrointestinal infection by bacteria that secrete ST and S-LT includes asymptomatic infection, nonbloody diarrhea, bloody diarrhea (hemorrhagic colitis), the hemolytic-uremia syndrome (HUS), thrombocytopenia purpura (TC), and death (Boyce T G, et al., 1995. *The New England Journal of Medicine,* 333 (6):364–368). ST and S-LT secreted in the intestinal lumen can be transported across the mucosa to circulation by transcytosis, where the toxin binds to and damages vascular endothelium and neuronal tissue. Circulating toxin results in a spectrum of pathologic events termed the hemolytic uremia syndrome (HUS). HUS is the most dreaded complication of toxin release and occurs in up to 10% of patients with this type of infection. It is most frequent in infants and the elderly, and is considered the most common cause of acute renal failure in children. Thrombocytopenia purpura is a similar condition typically diagnosed in adults, and is most likely HUS in infected individuals. HUS is characterized by microangiopathic hemolytic anemia, thrombocytopenia, renal-failure and central nervous system manifestations. The mortality rate for HUS is 3%–5%, and approximately 5% of surviving patients will have long-term renal and/or neurological damage.

Unfortunately, few antibiotics are clinically efficacious for Shigella infection, and resistance to first line antibiotic therapy (i.e., ampicilin) is increasing. Furthermore, antibiotic and anti-motility drugs are contraindicated for EHEC infections. Critically, there is no currently available treatment for HUS. Current management of HUS is restricted to supportive therapy and includes IV control of fluid and electrolyte balance, dialysis or transfusion. For these reasons new therapies are desperately needed. (Karen L. Kotloff, "Bacterial Diarrheal Pathogens. *Advances in Pediatric Infectious Diseases,* Vol. 14, Mosby, Inc. (1999)).

In principle, inhibiting the obligatory binding of the B pentamer of an $AB_5$ toxin to its glycolipid ligand could prevent the toxin-induced tissue destruction associated with infection by $AB_5$-toxigenic bacteria. However, the current belief in the field has been that this would be an ineffective approach for two reasons. First, monovalent oligosaccharides ligands have low binding affinity for proteins by which they are specifically bound. The standard view is well-characterized by the following statement: "The receptor-binding affinity of the individual B subunits for single ligands is relatively low; thus, a small molecule receptor analog cannot bind individual binding sites strongly enough to disable the toxin". (Donnelly et al., *Nature Medicine,* 2000. 6(3):257–258). Similarly, "Therapies might target the obligatory oligosaccharide-toxin recognition event, but the low intrinsic affinity of carbohydrate-protein interactions hampers the development of low-molecular-weight inhibitors" (Kitov P I, et. al., *Nature,* 2000. 403:669–672). As a consequence of this widely accepted view, current technologies propose to use the oligosaccharides in a polyvalent presentation to more closely mimic the presentation found on a target cell (Armstrong et al. "A Phase I Study of Chemically Synthesized Verotoxin (Shiga-like Toxin) Pk-trisaccharide Receptors Attached to Chromosorb for Preventing Hemolytic Uremia Syndrome" J. Inf. Dis. 171:1042–5 (1995), see also, U.S. Pat. No. 6,121,242).

A second difficulty associated with the use of a monovalent oligosaccharide ligand, specifically globotriose, has been cost-effective large scale synthesis. This problem has long been viewed as a major impediment to development of monovalent oligosaccharide based therapies (Walker W A, JPGN, March 2000).

In light of the above, new therapies are certainly required for the treatment of diseases and conditions caused by ST and S-LT. However, monovalent oligosaccharides have never been seriously considered as a possible treatment option until the present application.

All U.S. patents and publications referred to herein are hereby incorporated in their entirety by reference.

SUMMARY OF THE INVENTION

The present invention includes a composition comprising at least one monovalent oligosaccharide. The at least one monovalent oligosaccharide binds to Shiga-toxin and Shiga-like toxin. The composition may further comprise electrolytes, and the at least one monovalent oligosaccharide may be, for example, globotriose, galabiose, globotetraose or the Forssamm antigen. The composition may be administered parenterally (e.g., intravenously) or enterally (e.g., orally) and may be a pharmaceutical or nutritional composition, such as a rehydration solution.

Additionally, the present invention also encompasses a method of treating or preventing a condition in a mammal, caused by Shiga toxin or Shiga-like toxin. The method comprises administering to the mammal, in need of the treatment or prevention, the composition described above of, in an amount sufficient to effect the treatment or prevention. The condition may be, for example, hemorrhagic diarrhea, hemolytic uremia syndrome or thrombocytopenia purpura. The Shiga toxin may be produced, for example, by *Shigella dysenteria*. The Shiga-like toxin may be produced, for example, by *Escherichia coli*. The mammal may be, for example, a human or a mouse or another entity fitting within the definition of a mammal.

Furthermore, the present invention also encompasses a method of preventing binding of a Shiga toxin or Shiga-like toxin to a cellular receptor for the Shiga toxin or Shiga-like toxin comprising the step of exposing the Shiga toxin or Shiga-like toxin and the cellular receptor to at least one monovalent oligosaccharide such that the Shiga toxin or Shiga-like toxin binds to the monovalent oligosaccharide instead of to the cellular receptor. The monovalent oligosaccharide may be as described above.

Also, the present invention includes a method of reversing the binding of Shiga toxin or Shiga-like toxin to a cellular receptor comprising the step of exposing the bound cellular receptor to at least one monovalent oligosaccharide for a time and under conditions sufficient to effect the reverse binding.

Again, the monovalent oligosaccharide used may be that described above.

DETAILED DESCRIPTION OF THE INVENTION

As noted above, the subject invention relates to monovalent oligosaccharides (e.g., globotriose) which may be used to treat and prevent infections caused by bacterial toxins, in particular, Shiga toxins (STs) and Shiga-like toxins (S-LTs). For purposes of the present invention "monovalent" is defined as a single chemical unit with a free anomeric carbon which is not conjugated or bound to an inert matrix and which lacks a synthetic linking arm. An oligosaccharide is a sugar molecule that contains between 2–10 sugar units. The sugar units (i.e., $(CH_2O)_n$) in an oligosaccharide are connected by glycosidic linkages. Examples of monovalent oligosaccharides which may be utilized in the treatment and prevention of infections caused by STs or S-LTs include, for example, any soluble galα1,4gal compounds which occur naturally or are synthesized by chemical or enzymatic means, for example, galabiose, globotetraose, and Forssamm antigen. In particular, the use of the novel trisaccharide globotriose, also known as galactose α1,4galactose β1,4 glucose, is preferred. It should be noted, however, that any monovalent oligosaccharide which has the ability to be used to competitively inhibit binding of the toxins to their cellular targets and reverse binding once it has occurred is considered to fall within the scope of the present invention. Such oligosaccharides are usually readily soluble.

With respect to production, the monovalent oligosaccharides of the present invention may be made either recombinantly or synthetically. For example, U.S. Pat. No. 5,945,314 of Prieto et al., incorporated in its entirety by reference, describes a method of synthetically producing oligosaccharides. (See also U.S. Pat. No. 5,288,637.) For a discussion of recombinant production of a protein or oligosaccharide, see Sambrook et al., Molecular Cloning: A Laboratory Manual, 2d Edition, Cold Spring Harbor Laboratory Press (1989).

It should be noted that the monovalent oligosaccharides of the present invention may also be used to inhibit binding of non-Shiga toxins to cellular targets as well as Shiga-toxins. For example, the present monovalent oligosaccharides may be used to treat or neutralize any toxin causing hemorrhagic diarrhea or symptoms related thereto. These oligosaccharides may also be used in the prevention of symptoms caused by such conditions. For example, galα1,3gal may be used in treating the toxin produced by *C. difficile*, and globotetraose may be used in treating the toxin causing weanling pig edema.

In connection with hemolytic uremia and thrombocyopenia purpura, as mentioned above, the pathogenesis of these two conditions is dependent on the presence and action of ST or SLT. Inhibition of toxin activity, by binding to and destroying the endothelium, will prevent entry of the toxin into the circulation and subsequent damage. The saccharide's specific inhibition of Shigella or enterohemorrhagic *E. coli*'s toxin-binding to intestinal targets prevents progression of the disease to systemic toxemia.

In order to treat or prevent the conditions described above, the monovalent oligosaccharides may be administered a mammal (e.g., a human, a domestic animal or a non-domestic animal) via many different routes (e.g., enterally or parenterally). For example, the oligosaccharides may be utilized in a rehydration or hydration solution provided either orally (e.g., Pedialyte® or Equalyte®) or intravenously (e.g., saline/D5W). Such a solution may contain, for example, saline and/or glucose along with other electrolytes such as, for example, potassium, calcium and/or magnesium. Alternatively, the oligosaccharides may be added to a pre-made solution such as Pedialyte®.

Additionally, one or more monovalent oligosaccharides of the present invention may be utilized as an antibiotic or pharmaceutical along with a pharmaceutically acceptable carrier. A pharmaceutical carrier is any compatible, non-toxic substance suitable for delivering the oliogsaccharide(s) to the patient. Examples include sterile water, alcohol, fats, waxes, inert solids, phosphate buffered saline, oils, wetting agents or emulsions such as water/oil emulsions. The composition may be either in a liquid or solid form. For 10 example, the composition may be in the form of a tablet, capsule, intravenous liquid, or injectible. Proper fluidity can be maintained, for example, by the maintenance of the required particle size in the case of dispersions and by the use of surfactants. It may also be desirable to include isotonic agents, for example, other sugars and the like. Besides such inert diluents, the composition can also include adjuvants, such as wetting agents, emulsifying and suspending agents, sweetening agents, flavoring agents and perfuming agents.

Suspensions, in addition to the active oligosaccharide(s), may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art. For example, the monovalent oligosaccharides may be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant oligosaccharide(s).

Additionally, a homogenous mixture can be completely dispersed in water, admixed under sterile conditions with physiologically acceptable diluents, preservatives, buffers or propellants in order to form a spray or inhalant.

The dosage of the composition as well as the form and method of administration may be readily determined by one of ordinary skill in the art. If, for example, the composition is in liquid form, such as a hydration solution, approximately 0.1–100 mM of the oligosaccharide of choice should be present in the solution and preferably 2–10 mM of the oligosaccharide.

Further, the monovalent oligosaccharides may be administered as part of an antibiotic "cocktail" comprising several antibiotic agents or in conjunction with other agents being used to treat or prevent the symptoms caused by the bacteria-producing toxins.

Also, as noted above, the monovalent oligosaccharides of the present invention may be utilized in adults, children and domestic animals, but also may be used in agricultural livestock. For example, Shigella-like toxin causes a condition known as weanling pig edema disease, as noted above. More specifically, weanling pig edema results from a variant of SLT. This toxin, similar to SLT in humans, is absorbed from the intestinal enterocytes into the circulation where it attacks the vascular endothelium of multiple organs and the smooth muscle of small arteries and arterioles. Although this variant of SLT will bind globotriosylceramide, similar to its human counterparts, it prefers to bind globotetraosylceramide. Method of treatment of pig edema, using gal$\alpha$1,4gal, is analogous to treatment of hemolytic uremia syndrome using this same oligosaccharide. In particular, the saccharide can competitively inhibit the binding of toxin to its intestinal target and thus prevent absorption of toxin into the bloodstream. Thus, the oligosaccharides of the present invention should also prove useful in preventing and treating weanling pig edema disease as well as human conditions. Currently, there are no treatments for weanling pig edema disease.

Additionally, it should be noted that the present monovalent oligosaccharides, for example, globotriose, should not cause significant side effects. In particular, globotriose is not metabolized by the body, thereby preventing formation of metabolites. Rather, it is rapidly cleared through the kidneys. Also, since there is endogenous expression of gal$\alpha$1,4 motifs in the body, the monovalent oligosaccharides should not give rise to an undesirable immunogenic reaction. Thus, the pharmocokinetic profile of globotriose, coupled with its lack of toxic side effects, make it particularly well-suited as an effective treatment of, for example, HUS or other conditions caused by STs or SLTs.

In terms of method of action, the monovalent oligosaccharides prevent binding of the toxin in question to the cellular target by binding to the toxin itself, thereby preventing the toxin from binding to the cellular receptor. In particular, the unconjugated monovalent oligosaccharides of the present invention and, in particular, the gal$\alpha$1,4 gal saccharides competitively inhibit toxin by serving as alternative toxin receptors as opposed to the receptors on the glycolipid surface of the target cells. Additionally, if binding has already occurred between the toxin and cellular receptor, the monovalent oligosaccharide is able to reverse this binding.

In addition to pharmaceutical compositions, the present invention includes nutritional compositions. Such compositions, for purposes of the present invention, include any food or preparation for human consumption including for enteral or parenteral consumption, which when taken into the body (a) serve to nourish or build up tissues or supply energy and/or (b) maintain, restore or support adequate nutritional status or metabolic function.

The nutritional compositions of the present invention comprise at least one monovalent oligosaccharide (e.g., globotriose) utilized to treat or prevent conditions associated with the above toxins, and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany certain metabolic conditions (e.g., metabolic disorders).

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed search. Additionally, examples of proteins which may be utilized in the nutritional composition of the invention include but are not limited to soy proteins, electrodialysed whey, electrodialysed skim milk, milk whey, or the hydrolysates of these proteins.

With respect to vitamins and minerals, the following may be added to the nutritional compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the nutritional compositions of the present invention will be of semi-purified or purified origin. By semi-purified or purified is meant a material which has been prepared by purification of a natural material or by synthesis.

Examples of nutritional compositions of the present invention include but are not limited to infant formulas, dietary supplements, dietary substitutes, and rehydration compositions, the latter of which may also be considered as pharmaceutical compositions. Nutritional compositions of particular interest include but are not limited to those utilized for enteral and parenteral supplementation for infants, specialist infant formulas, supplements for the elderly, and supplements for those with gastrointestinal difficulties and/or malabsorption. Certainly the young, the elderly, and the immunocompromised are particularly susceptible to suffering serious, and even fatal, effects from the toxins.

The nutritional compositions of the present invention may also be added to food even when supplementation of the diet is not required. For example, the composition may be added to food of any type including but not limited to margarines, modified butters, cheeses, milk, yogurt, chocolate, candy, snacks, salad oils, cooking oils, cooking fats, meats, fish and beverages.

In a preferred embodiment of the present invention, the nutritional composition is an enteral nutritional product, more preferably, an adult or pediatric enteral nutritional product. For example, this composition may be administered to adults or children experiencing gastrointestinal distress or having specialized needs due to chronic or acute disease states. The composition may comprise, produced in accordance with the present invention, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art. (See also the Examples below.)

The enteral formula, for example, may be sterilized and subsequently utilized on a ready-to-feed (RTF) basis or stored in a concentrated liquid or lyophilized powder form. The powder can be prepared by spray drying the formula prepared as indicated above, and reconstituting it by rehydrating the concentrate. Adult and pediatric nutritional formulas are well known in the art and are commercially available (e.g., Similac®, Ensure®, Jevity® and Alimentum® from Ross Products Division, Abbott Laboratories, Columbus, Ohio).

The energy density of the nutritional compositions of the present invention, when in liquid form, may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 660 mOsm.

The nutritional formula may include macronutrients, vitamins, and minerals, as noted above, in addition to the monovalent oligosaccharides of the present invention. The presence of these additional components helps the individual ingest the minimum daily requirements of these elements. In addition, it may also be desirable to add zinc, copper, folic acid and antioxidants to the composition. It is believed that these substance boost a stressed immune system and will therefore provide further benefits to the individual receiving the composition. A pharmaceutical composition, as described above, may also be supplemented with these elements.

In a more preferred embodiment, the nutritional composition comprises, in addition to antioxidants and at least one monovalent oligosaccharide, a source of carbohydrate wherein at least 5 weight percent of the carbohydrate is indigestible oligosaccharide. In a more preferred embodiment, the nutritional composition additionally comprises protein, taurine, and carnitine.

The present invention may be illustrated by the use of the following non-limiting examples:

EXAMPLE I

Effects of Globotriose in vitro and in vivo

Previous pharmacokinetic studies by the present scientists have demonstrated that globotriose may be administered to mice orally (3333 mg/kg) or intravenously (333 mg/kg) with no toxic effects. IV administered globotriose demonstrated bi-exponential clearance kinetics signifying that it is diluted into the extracellular fluid of the body and slowly excreted through the kidneys over time (>24 hours). Orally administered globotriose likewise demonstrated bi-exponential kinetics, was approximately 10% bioavailable (10% of oral dose crossed into circulation) and was excreted in the urine up to 48 hours post-dose. The majority of orally administered globotriose was excreted into the feces unmetabolized.

In vitro experiments conducted by the present scientists have demonstrated that globotriose is able to inhibit the cytotoxic effects of Shiga-like toxins I and II (SLT I and II). More specifically, Vero cells (normal adult monkey kidney epithelial cells) were incubated for 24 hours at 37° C. with a LD50 dose of diluted E. coli O157:H7 culture supernatant alone or in simultaneous combination with 5%, 2.5%, or 1.25% globotriose. After the 24-hour incubation, cells were washed twice in PBS and then fixed for two minutes in 2% paraformaldehyde. Viable cells were detected by staining with 0.13% crystal violet for ten minutes. Excess stain was removed by several water washes and 25 minutes of 50% ethanol washes. Results were quantified by eluting the crystal violet dye for 10 minutes with 50% ethanol and reading the absorbance at 600 nm with a Thermomax plate reader [Molecular Devices, Menlo City, Calif.].

Figure 1A:
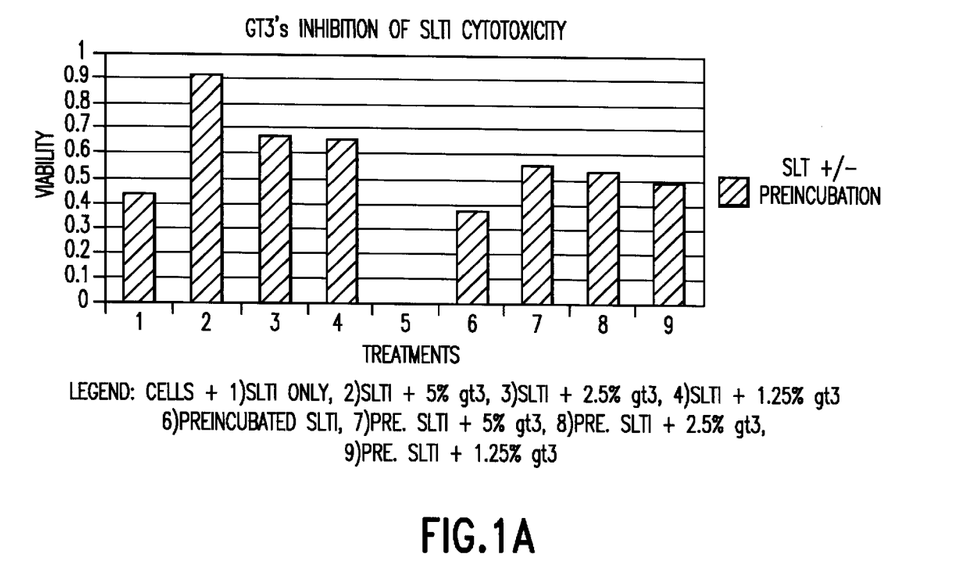
FIG. 1A and 1B illustrates in vitro data that demonstrate the ability of a monovalent oligosaccharide (i.e., globotriose) to prevent and reverse binding of S-LT to target cells.
Figure 1B:
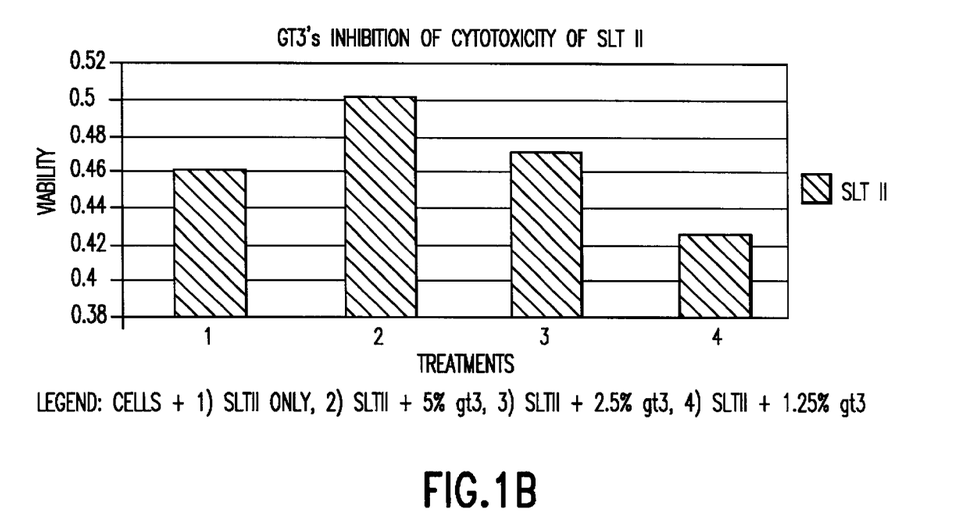
Figure 2:
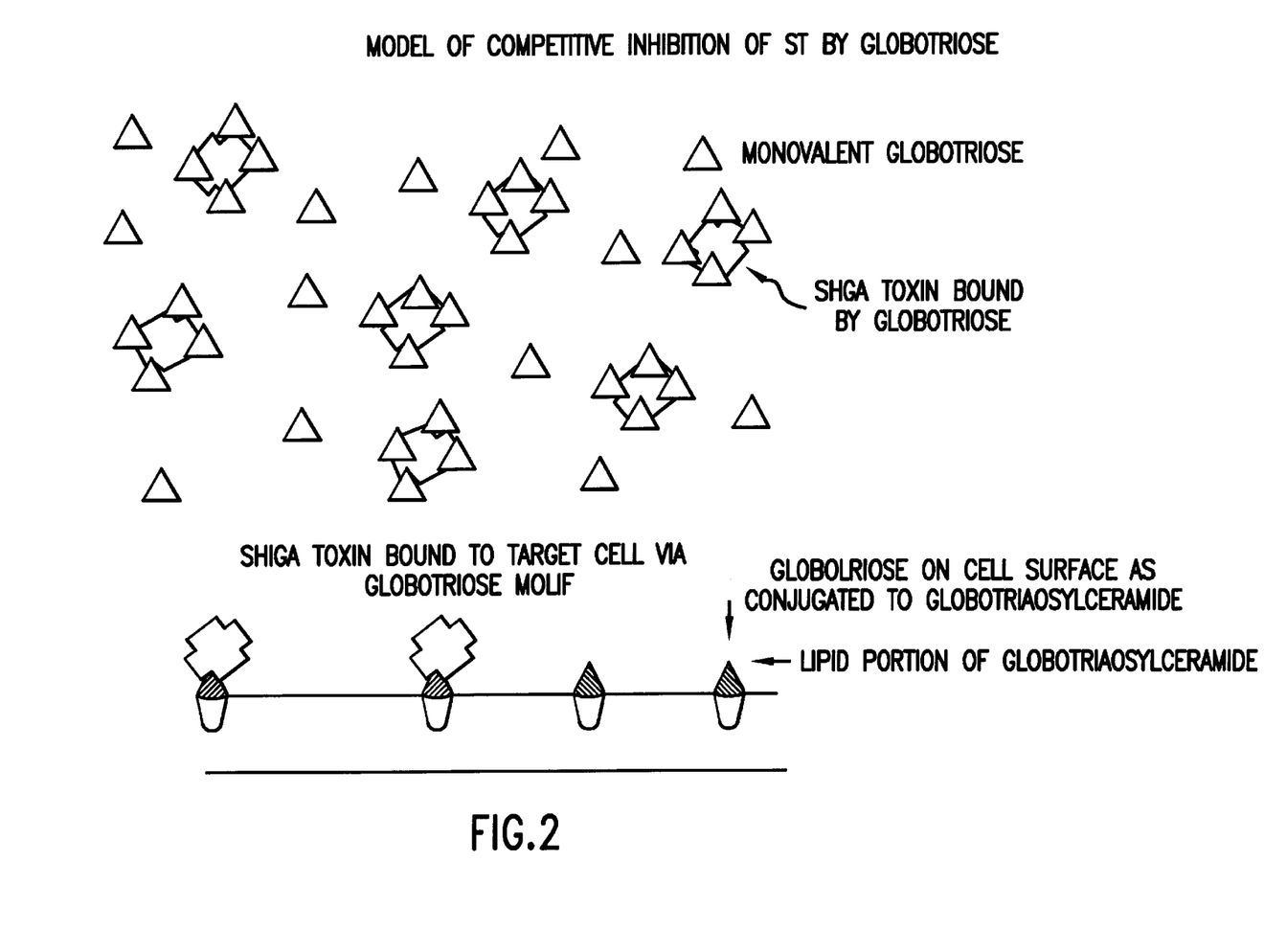
FIG. 2 represents a model of competitive inhibition of ST by globotriose.
Figure 3:
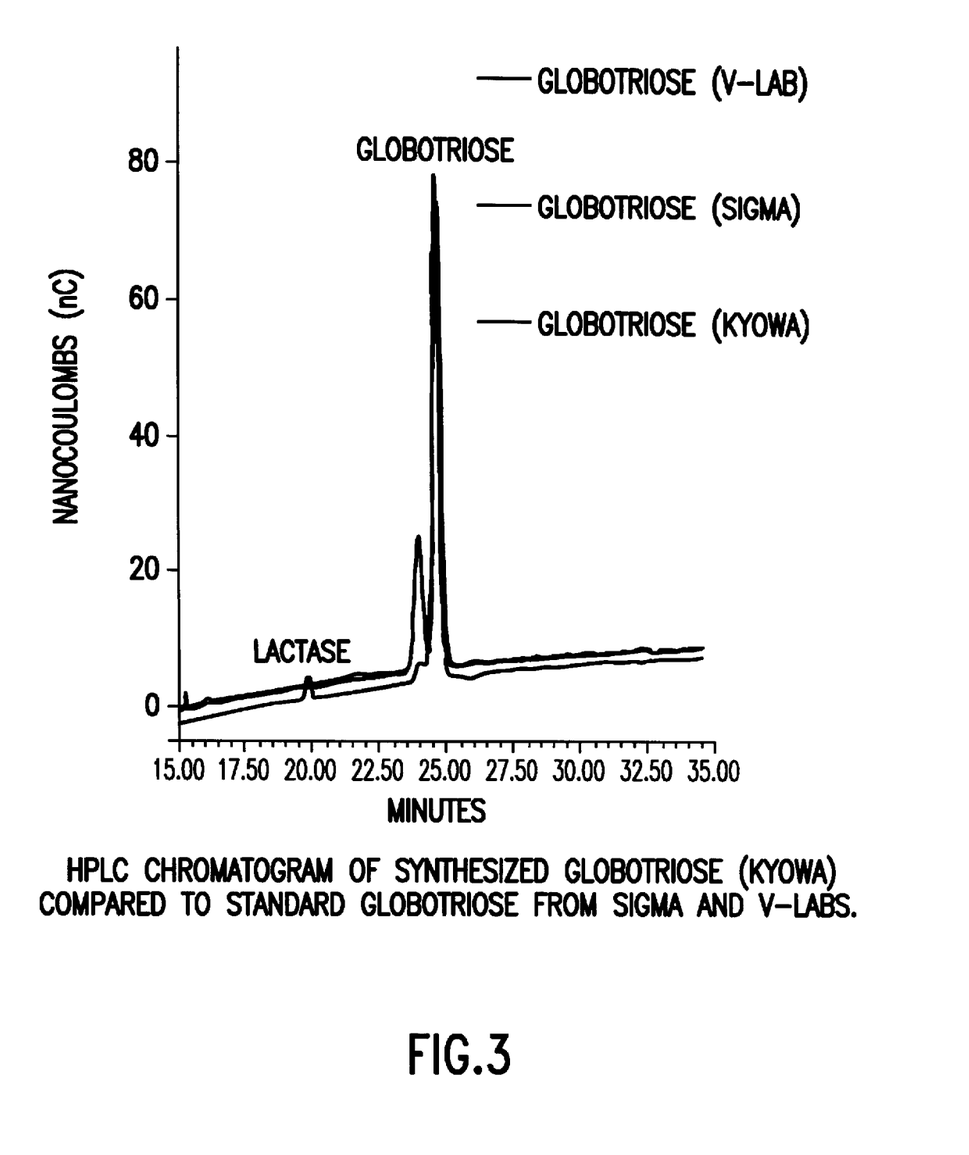
FIG. 3 chromatogram of the monovalent oligosaccharides globotriose.

Globotriose partially inhibited cell death from both toxins in a dose related manner (8% inhibition of SLT II and 52% of SLT I at the 5% dose). To further test the marked 20 effect on SLT I, cells were preincubated with LD50 dilution of culture supernatant for 30 minutes at 37° C. to allow the toxin to attach to the cells. Next, naive media or globotriose (5%, 2.5%, 1.25%) was added to the cells and toxin for a 24-hour incubation at 370 C. Globotriose was also an effective inhibitor under these conditions, reducing cytotoxicity by 33% at the 5% globotriose dose level. (See FIG. 1.)

EXAMPLE II

Effects of Globotriose on Inhibition of Attachment of Bacterial Toxin to Intestinal Cells In vitro observations may be applied to an in vivo model. More specifically, streptomycin treated (in order to remove normal gut flora) mice are orally inoculated with $10^7$ E. coli O157:H7 organisms and animals dosed orally or intravenously with globotriose are compared to animals dosed with saline. Past studies have shown that untreated animals will die within 4–6 days of inoculation unless effectively treated (Wadolkowski et al, *Infection and Immunity* Vol 58 No.12 3959–3965, Dec.1990, Paton et al., *Nature Medicine* Vol 6 No. 3 265–270 March 2000). Animals dosed with globotriose daily for 14 days post O157:H7 inoculation may demonstrate improved survival to control animals dosed with saline. In particular, globotriose may inhibit attachment of bacterial toxin to intestinal cells, reducing the amount of toxin entering the circulation, and thereby inhibiting death.

As noted above, the monovalent oligosaccharides may be added to infant formulas and other known nutritional compositions. Examples of such products are as follows:

I. Infant Formulations

A. Isomil® Soy Formula with Iron

Usage: As a beverage for infants, children and adults with an allergy or sensitivity to cows milk. A feeding for patients with disorders for which lactose should be avoided: lactase deficiency, lactose intolerance and galactosemia.

Features

Soy protein isolate to avoid symptoms of cow's-milk-protein allergy or sensitivity.

Lactose-free formulation to avoid lactose-associated diarrhea.

Low osmolality (240 mOs/kg water) to reduce risk of osmotic diarrhea.

Dual carbohydrates (corn syrup and sucrose) designed to enhance carbohydrate absorption and reduce the risk of exceeding the absorptive capacity of the damaged gut.

1.8 mg of Iron (as ferrous sulfate) per 100 Calories to help prevent iron deficiency.

Recommended levels of vitamins and minerals.

Vegetable oils to provide recommended levels of essential fatty acids.

Milk-white color, milk-like consistency and pleasant aroma.

Ingredients: (Pareve) 85% water, 4.9% corn syrup, 2.6% sugar (sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and disglycerides, soy lecithin, carrageenan, ascorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

B. Isomil® DF Soy Formula for Diarrhea

Usage: As a short-term feeding for the dietary management of diarrhea in infants and toddlers.

Features

First infant formula to contain added dietary fiber from soy fiber specifically for diarrhea management.

Clinically shown to reduce the duration of loose, watery stools during mild to severe diarrhea in infants.

Nutritionally complete to meet the nutritional needs of the infant.

Soy protein isolate with added L-methionine meets or exceeds an infant's requirement for all essential amino acids.

Lactose-free formulation to avoid lactose-associated diarrhea.

Low osmolality (240 mOsm/kg water) to reduce the risk of osmotic diarrhea.

Dual carbohydrates (corn syrup and sucrose) designed to enhance carbohydrate absorption and reduce the risk of exceeding the absorptive capacity of the damaged gut.

Meets or exceeds the vitamin and mineral levels recommended by the Committee on Nutrition of the American Academy of Pediatrics and required by the Infant Formula Act.

1.8 mg of iron (as ferrous sulfate) per 100 Calories to help prevent iron deficiency.

Vegetable oils to provide recommended levels of essential fatty acids.

Ingredients: (Pareve) 86% water, 4.8% corn syrup, 2.5% sugar (sucrose), 2.1% soy oil, 2.0% soy protein isolate, 1.4% coconut oil, 0.77% soy fiber, 0.12% calcium citrate, 0.11% calcium phosphate tribasic, 0.10% potassium citrate, potassium chloride, potassium phosphate monobasic, mono and diglycerides, soy lecithin, carrageenan, magnesium chloride, ascorbic acid, L-methionine, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

C. Isomil® SF Sucrose-Free Soy Formula with Iron

Usage: As a beverage for infants, children and adults with an allergy or sensitivity to cow's-milk protein or an intolerance to sucrose. A feeding for patients with disorders for which lactose and sucrose should be avoided.

Features

Soy protein isolate to avoid symptoms of cow's-milk-protein allergy or sensitivity.

Lactose-free formulation to avoid lactose-associated diarrhea (carbohydrate source is Polycose® Glucose Polymers).

Sucrose free for the patient who cannot tolerate sucrose.

Low osmolality (180 mOsm/kg water) to reduce risk of osmotic diarrhea.

1.8 mg of iron (as ferrous sulfate) per 100 Calories to help prevent iron deficiency.

Recommended levels of vitamins and minerals.

Vegetable oils to provide recommended levels of essential fatty acids.

Milk-white color, milk-like consistency and pleasant aroma.

Ingredients: (Pareve) 75% water, 11.8% hydrolized cornstarch, 4.1% soy oil, 4.1% soy protein isolate, 2.8% coconut oil, 1.0% modified cornstarch, 0.38% calcium phosphate tribasic, 0.17% potassium citrate, 0.13% potassium chloride, mono- and diglycerides, soy lecithin, magnesium chloride, abscorbic acid, L-methionine, calcium carbonate, sodium chloride, choline chloride, carrageenan, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

D. Isomil® Soy Formula with Iron Ready to Feed, 20 Cal/fl oz.:

Usage: When a soy feeding is desired.

Ingredients: (Pareve) 85% water, 4.9% corn syrup, 2.6% sugar(sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and diglycerides, soy lecithin, carrageenan, abscorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

E. Similac® Infant Formula

Usage: When an infant formula is needed: if the decision is made to discontinue breastfeeding before age 1 year, if a supplement to breastfeeding is needed or as a routine feeding if breastfeeding is not adopted.

Features

Protein of appropriate quality and quantity for good growth; heat-denatured, which reduces the risk of milk-associated enteric blood loss.

Fat from a blend of vegetable oils (doubly homogenized), providing essential linoleic acid that is easily absorbed.

Carbohydrate as lactose in proportion similar to that of human milk.

Low renal solute load to minimize stress on developing organs.

Powder, Concentrated Liquid and Ready To Feed forms.

Ingredients: (-D) Water, nonfat milk, lactose, soy oil, coconut oil, mono- and diglycerides, soy lecithin, abscorbic acid, carrageenan, choline chloride, taurine, m-inositol, alpha-tocopheryl acetate, zinc sulfate, niacinamide, ferrous sulfate, calcium pantothenate, cupric sulfate, vitamin A palmitate, thiamine chloride hydrochloride, riboflavin, pyridoxine hydrochloride, folio acid, manganese sulfate, phylloquinone, biotin, sodium selenite, vitamin D3 and cyanocobalamin.

F. Similac® NeoCare Premature Infant Formula with Iron

Usage: For premature infants' special nutritional needs after hospital discharge. Similac NeoCare is a nutritionally complete formula developed to provide premature infants with extra calories, protein, vitamins and minerals needed to promote catch-up growth and support development.

Features

Reduces the need for caloric and vitamin supplementation. More calories (22 Cal/fl oz) than standard term formulas (20 Cal/fl oz).

Highly absorbed fat blend, with medium-chain triglycerides (MCT oil) to help meet the special digestive needs of premature infants.

Higher levels of protein, vitamins and minerals per 100 calories to extend the nutritional support initiated in-hospital.

More calcium and phosphorus for improved bone mineralization.

Ingredients: -D Corn syrup solids, nonfat milk, lactose, whey protein concentrate, soy oil, high-oleic safflower oil, fractionated coconut oil (medium chain triglycerides), coconut oil, potassium citrate, calcium phosphate tribasic, calcium carbonate, ascorbic acid, magnesium chloride, potassium chloride, sodium chloride, taurine, ferrous sulfate, m-inositol, choline chloride, ascorbyl palmitate, L-carnitine, alpha-tocopheryl acetate, zinc sulfate, niacinamide, mixed tocopherols, sodium citrate, calcium pantothenate, cupric sulfate, thiamine chloride hydrochloride, vitamin A palmitate, beta carotene, riboflavin, pyridoxine hydrochloride, folic acid, manganese sulfate, phylloquinone, biotin, sodium selenite, vitamin D3 and cyanocobalamin.

G. Similac Natural Care Low-Iron Human Milk Fortifier Ready to Use, 24 Cal/fl oz.

Usage: Designed to be mixed with human milk or to be fed alternatively with human milk to low-birth-weight infants.

Ingredients: -D Water, nonfat milk, hydrolyzed cornstarch, lactose, fractionated coconut oil (medium-chain triglycerides), whey protein concentrate, soy oil, coconut oil, calcium phosphate tribasic, potassium citrate, magnesium chloride, sodium citrate, ascorbic acid, calcium carbonate, mono and diglycerides, soy lecithin, carrageenan, choline chloride, m-inositol, taurine, niacinamide, L-carnitine, alpha tocopheryl acetate, zinc sulfate, potassium chloride, calcium pantothenate, ferrous sulfate, cupric sulfate, riboflavin, vitamin A palmitate, thiamine chloride hydrochloride, pyridoxine hydrochloride, biotin, folic acid, manganese sulfate, phylloquinone, vitamin D3, sodium selenite and cyanocobalamin.

Various PUFAs of this invention can be substituted and/or added to the infant formulae or solutions described above and below, and to other infant formulae known to those in the art.

H. Rehydralyte® Oral Electrolyte Rehydration Solution

Usage: For the replacement of water and electrolyte deficits in mild to moderate dehydration secondary to acute diarrhea in infants and children. Ingredients: (Pareve) Water, dextrose, sodium chloride, potassium citrate, and sodium citrate.

I. Pedialyte® Oral Electrolyte Maintenance Solution

Usage: 1) For maintenance of water and electrolytes and prevention of dehydration secondary to acute diarrhea in infants and children. 2) For maintenance of water and electrolytes following corrective parenteral therapy for severe dehydration.

Ingredients: Unflavored Pedialyte: (Pareve) Water, dextrose, potassium citrate, sodium chloride and sodium citrate Flavored Pedialyte: (Pareve) Water, dextrose, natural and artificial flavors (natural punch flavor, artificial cherry flavor, natural and artificial almond extract, artificial orange flavor, natural tropical fruit flavor, natural vanilla flavor), potassium citrate, sodium chloride and sodium citrate.

II. Nutritional Formulations

A. Ensure®

Usage: ENSURE is a low-residue liquid food designed primarily as an oral nutritional supplement to be used with or between meals or, in appropriate amounts, as a meal replacement. ENSURE is lactose- and gluten-free, and is suitable for use in modified diets, including low-cholesterol diets. Although it is primarily an oral supplement, it can be fed by tube.

Paticute Conditive

For patients on modified diets

For elderly patients at nutrition risk

For patients with involuntary weight loss

For patients recovering from illness or surgery

For patients who need a low-residue diet

Ingredients: -D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate.

B. Ensure® Bars

Usage: ENSURE BARS are complete, balanced nutrition for supplemental use between or with meals. They provide a delicious, nutrient-rich alternative to other snacks. ENSURE BARS contain <1 g lactose/bar, and Chocolate Fudge Brownie flavor is gluten-free. (Honey Graham Crunch flavor contains gluten.)

Patient Conditions

For patients who need extra calories, protein, vitamins and minerals.

Especially useful for people who do not take in enough calories and nutrients.

For people who have the ability to chew and swallow

Not to be used by anyone with a peanut allergy or any type of allergy to nuts.

Ingredients: Honey Graham Crunch—High-Fructose Corn Syrup, Soy Protein Isolate, Brown Sugar, Honey, Maltodextrin (Corn), Crisp Rice (Milled Rice, Sugar [Sucrose], Salt [Sodium Chloride] and Malt), Oat Bran, Partially Hydrogenated Cottonseed and Soy Oils, Soy Polysaccharide, Glycerine, Whey Protein Concentrate, Polydextrose, Fructose, Calcium Caseinate, Cocoa Powder, Artificial Flavors, Canola Oil, High-Oleic Safflower Oil, Nonfat Dry Milk, Whey Powder, Soy Lecithin and Corn Oil. Manufactured in a facility that processes nuts.

Vitamins and Minerals: Calcium Phosphate Tribasic, Potassium Phosphate Dibasic, Magnesium Oxide, Salt (Sodium Chloride), Potassium Chloride, Ascorbic Acid, Ferric Orthophosphate, Alpha-Tocopheryl Acetate, Niacinamide, Zinc Oxide, Calcium Pantothenate, Copper Gluconate, Manganese Sulfate, Riboflavin, Beta Carotene, Pyridoxine Hydrochloride, Thiamine Mononitrate, Folic Acid, Biotin, Chromium Chloride, Potassium Iodide, Sodium Selenate, Sodium Molybdate, Phylloquinone, Vitamin D3 and Cyanocobalamin.

Protein: Honey Graham Crunch—The protein source is a blend of soy protein isolate and milk proteins.

| Soy protein isolate | 74% |
|---|---|
| Milk proteins | 26% |

Fat: Honey Graham Crunch—The fat source is a blend of partially hydrogenated cottonseed and soybean, canola, high oleic safflower, oils, and soy lecithin.

| Partially hydrogenated cottonseed and soybean oil | 76% |
|---|---|
| Canola oil | 8% |
| High-oleic safflower oil | 8% |
| Corn oil | 4% |
| Soy lecithin | 4% |

Carbohydrate: Honey Graham Crunch—The carbohydrate source is a combination of high-fructose corn syrup, brown sugar, maltodextrin, honey, crisp rice, glycerine, soy polysaccharide, and oat bran.

| High-fructose corn syrup | 24% |
|---|---|
| Brown sugar | 21% |
| Maltodextrin | 12% |
| Honey | 11% |
| Crisp rice | 9% |
| Glycerine | 9% |
| Soy Polysaccharide | 7% |
| Oat bran | 7% |

C. Ensure® High Protein

Usage: ENSURE HIGH PROTEIN is a concentrated, high-protein liquid food designed for people who require additional calories, protein, vitamins, and minerals in their diets. It can be used as an oral nutritional supplement with or between meals or, in appropriate amounts, as a meal replacement. ENSURE HIGH PROTEIN is lactose- and gluten-free, and is suitable for use by people recovering from general surgery or hip fractures and by patients at risk for pressure ulcers.

Patient Conditions

For patients who require additional calories, protein, vitamins, and minerals, such as patients recovering from general surgery or hip fractures, patients at risk for pressure ulcers, and patients on low-cholesterol diets Features Low in saturated fat Contains 6 g of total fat and <5 mg of cholesterol per serving Rich, creamy taste Excellent source of protein, calcium, and other essential vitamins and minerals For low-cholesterol diets Lactose-free, easily digested Ingredients Vanilla Supreme: -D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate, Phylloquinone, Vitamin D3 and Cyanocobalamin.

Protein

The protein source is a blend of two high-biologic-value proteins: casein and soy.

| Sodium and calcium caseinates | 85% |
|---|---|
| Soy protein isolate | 15% |

Fat

The fat source is a blend of three oils: high-oleic safflower, canola, and soy.

| | |
|---|---|
| High-oleic safflower oil | 40% |
| Canola oil | 30% |
| Soy oil | 30% |

The level of fat in ENSURE HIGH PROTEIN meets American Heart Association (AHA) guidelines. The 6 grams of fat in ENSURE HIGH PROTEIN represent 24% of the total calories, with 2.6% of the fat being from saturated fatty acids and 7.9% from polyunsaturated fatty acids. These values are within the AHA guidelines of <30% of total calories from fat, <10% of the calories from saturated fatty acids, and <10% of total calories from polyunsaturated fatty acids.

Carbohydrate

ENSURE HIGH PROTEIN contains a combination of maltodextrin and sucrose. The mild sweetness and flavor variety (vanilla supreme, chocolate royal, wild berry, and banana), plus VARI-FLAVORS® Flavor Pacs in pecan, cherry, strawberry, lemon, and orange, help to prevent flavor fatigue and aid in patient compliance.

Vanilla and Other Nonchocolate Flavors

| | |
|---|---|
| Sucrose | 60% |
| Maltodextrin | 40% |

Chocolate

| | |
|---|---|
| Sucrose | 70% |
| Maltodextrin | 30% |

D. Ensure® Light

Usage: ENSURE LIGHT is a low-fat liquid food designed for use as an oral nutritional supplement with or between meals. ENSURE LIGHT is lactose- and gluten-free, and is suitable for use in modified diets, including low-cholesterol diets.

Patient Conditions

For normal-weight or overweight patients who need extra nutrition in a supplement that contains 50% less fat and 20% fewer calories than ENSURE.

For healthy adults who don't eat right and need extra nutrition.

Features

Low in fat and saturated fat
Contains 3 g of total fat per serving and <5 mg cholesterol
Rich, creamy taste
Excellent source of calcium and other essential vitamins and minerals
For low-cholesterol diets
Lactose-free, easily digested

Ingredients

French Vanilla: -D Water, Maltodextrin (Corn), Sugar (Sucrose), Calcium Caseinate, High-Oleic Safflower Oil, Canola Oil, Magnesium Chloride, Sodium Citrate, Potassium Citrate, Potassium Phosphate Dibasic, Magnesium Phosphate Dibasic, Natural and Artificial Flavor, Calcium Phosphate Tribasic, Cellulose Gel, Choline Chloride, Soy Lecithin, Carrageenan, Salt (Sodium Chloride), Ascorbic Acid, Cellulose Gum, Ferrous Sulfate, Alpha-Tocopheryl Acetate, Zinc Sulfate, Niacinamide, Manganese Sulfate, Calcium Pantothenate, Cupric Sulfate, Thiamine Chloride Hydrochloride, Vitamin A Palmitate, Pyridoxine Hydrochloride, Riboflavin, Chromium Chloride, Folic Acid, Sodium Molybdate, Biotin, Potassium Iodide, Sodium Selenate, Phylloquinone, Vitamin D3 and Cyanocobalamin

Protein

The protein source is calcium caseinate.

Calcium caseinate 100%

Fat

The fat source is a blend of two oils: high-oleic safflower and canola.

| | |
|---|---|
| High-oleic safflower oil | 70% |
| Canola oil | 30% |

The level of fat in ENSURE LIGHT meets American Heart Association (AHA) guidelines. The 3 grams of fat in ENSURE LIGHT represent 13.5% of the total calories, with 1.4% of the fat being from saturated fatty acids and 2.6% from polyunsaturated fatty acids. These values are within the AHA guidelines of <30% of total calories from fat, <10% of the, calories from saturated fatty acids, and <10% of total calories from polyunsaturated fatty acids.

Carbohydrate

ENSURE LIGHT contains a combination of maltodextrin and sucrose. The chocolate flavor contains corn syrup as well. The mild sweetness and flavor variety (French vanilla, chocolate supreme, strawberry swirl), plus VARI-FLAVORS® Flavor Pacs in pecan, cherry, strawberry, lemon, and orange, help to prevent flavor fatigue and aid in patient compliance.

Vanilla and Other Nonchocolate Flavors

| | |
|---|---|
| Sucrose | 51% |
| Maltodextrin | 49% |

Chocolate

| | |
|---|---|
| Sucrose | 47.0% |
| Corn Syrup | 26.5% |
| Maltodextrin | 26.5% |

Vitamins and Minerals

An 8-fl-oz serving of ENSURE LIGHT provides at least 25% of the RDIs for 24 key vitamins and minerals.

Caffeine

Chocolate flavor contains 2.1 mg caffeine/8 fl oz.

E. Ensure Plus®

Usage: ENSURE PLUS is a high-calorie, low-residue liquid food for use when extra calories and nutrients, but a normal concentration of protein, are needed. It is designed primarily as an oral nutritional supplement to be used with or between meals or, in appropriate amounts, as a meal replacement. ENSURE PLUS is lactose- and gluten-free. Although it is primarily an oral nutritional supplement, it can be fed by tube.

Patient Conditions

For patients who require extra calories and nutrients, but a normal concentration of protein, in a limited volume For patients who need to gain or maintain healthy weight Features Rich, creamy taste Good source of essential vitamins and minerals Ingredients Vanilla: -D Water, Corn Syrup, Maltodextrin (Corn), Corn Oil, Sodium and Calcium Caseinates, Sugar (Sucrose), Soy Protein Isolate, Magnesium Chloride, Potassium Citrate, Calcium Phosphate Tribasic, Soy Lecithin, Natural and Artificial Flavor, Sodium Citrate, Potassium Chloride, Choline Chloride, Ascorbic Acid, Carrageenan, Zinc Sulfate, Ferrous Sulfate, Alpha-Tocopheryl Acetate, Niacinamide, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

Protein

The protein source is a blend of two high-biologic-value proteins: casein and soy.

| | |
|---|---|
| Sodium and calcium caseinates | 84% |
| Soy protein isolate | 16% |

Fat

The fat source is corn oil.

Corn oil 100%

Carbohydrate

ENSURE PLUS contains a combination of maltodextrin and sucrose. The mild sweetness and flavor variety (vanilla, chocolate, strawberry, coffee, buffer pecan, and eggnog), plus VARI-FLAVORS® Flavor Pacs in pecan, cherry, strawberry, lemon, and orange, help to prevent flavor fatigue and aid in patient compliance.

Vanilla, Strawberry, Butter Pecan, and Coffee Flavors

| | |
|---|---|
| Corn Syrup | 39% |
| Maltodextrin | 38% |
| Sucrose | 23% |

Chocolate and Eggnog Flavors

| | |
|---|---|
| Corn Syrup | 36% |
| Maltodextrin | 34% |
| Sucrose | 30% |

Vitamins and Minerals

An 8-fl-oz serving of ENSURE PLUS provides at least 15% of the RDIs for 25 key Vitamins and minerals.

Caffeine

Chocolate flavor contains 3.1 mg Caffeine/8 fl oz. Coffee flavor contains a trace amount of caffeine.

F. Ensure Plus® HN

Usage: ENSURE PLUS HN is a nutritionally complete high-calorie, high-nitrogen liquid food designed for people with higher calorie and protein needs or limited volume tolerance. It may be used for oral supplementation or for total nutritional support by tube. ENSURE PLUS HN is lactose- and gluten-free.

Patient Conditions

For patients with increased calorie and protein needs, such as following surgery or injury.

For patients with limited volume tolerance and early satiety.

Features

For supplemental or total nutrition

For oral or tube feeding 1.5 CaVmL,

High nitrogen

Calorically dense

Ingredients

Vanilla: -D Water, Maltodextrin (Corn), Sodium and Calcium Caseinates, Corn Oil, Sugar (Sucrose), Soy Protein Isolate, Magnesium Chloride, Potassium Citrate, Calcium Phosphate Tribasic, Soy Lecithin, Natural and Artificial Flavor, Sodium Citrate, Choline Chloride, Ascorbic Acid, Taurine, L-Carnitine, Zinc Sulfate, Ferrous Sulfate, Alpha-Tocopheryl Acetate, Niacinamide, Carrageenan, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

G. Ensure® Powder

Usage: ENSURE POWDER (reconstituted with water) is a low-residue liquid food designed primarily as an oral nutritional supplement to be used with or between meals. ENSURE POWDER is lactose- and gluten-free, and is suitable for use in modified diets, including low-cholesterol diets.

Patient Conditions

For patients on modified diets

For elderly patients at nutrition risk

For patients recovering from illness/surgery

For patients who need a low-residue diet

Features

Convenient, easy to mix
Low in saturated fat
Contains 9 g of total fat and <5 mg of cholesterol per serving
High in vitamins and minerals
For low-cholesterol diets
Lactose-free, easily digested
Ingredients: -D Corn Syrup, Maltodextrin (Corn), Sugar (Sucrose), Corn Oil, Sodium and Calcium Caseinates, Soy Protein Isolate, Artificial Flavor, Potassium Citrate, Magnesium Chloride, Sodium Citrate, Calcium Phosphate Tribasic, Potassium Chloride, Soy Lecithin, Ascorbic Acid, Choline Chloride, Zinc Sulfate, Ferrous Sulfate, Alpha-Tocopheryl Acetate, Niacinamide, Calcium Pantothenate, Manganese Sulfate, Thiamine Chloride Hydrochloride, Cupric Sulfate, Pyridoxine Hydrochloride, Riboflavin, Vitamin A Palmitate, Folic Acid, Biotin, Sodium Molybdate, Chromium Chloride, Potassium Iodide, Sodium Selenate, Phylloquinone, Vitamin D3 and Cyanocobalamin.

Protein

The protein source is a blend of two high-biologic-value proteins: casein and soy.

| | |
|---|---|
| Sodium and calcium caseinates | 84% |
| Soy protein isolate | 16% |

Fat

The fat source is corn oil.
Corn oil 100%

Carbohydrate

ENSURE POWDER contains a combination of corn syrup, maltodextrin, and sucrose. The mild sweetness of ENSURE POWDER, plus VARI-FLAVORS® Flavor Pacs in pecan, cherry, strawberry, lemon, and orange, helps to prevent flavor fatigue and aid in patient compliance.

Vanilla

| | |
|---|---|
| Corn Syrup | 35% |
| Maltodextrin | 35% |
| Sucrose | 30% |

H. Ensure® Pudding

Usage: ENSURE PUDDING is a nutrient-dense supplement providing balanced nutrition in a nonliquid form to be used with or between meals. It is appropriate for consistency-modified diets (e.g., soft, pureed, or full liquid) or for people with swallowing impairments. ENSURE PUDDING is gluten-free.

Patient Conditions

For patients on consistency-modified diets (e.g., soft, pureed, or full liquid)
For patients with swallowing impairments Features Rich and creamy, good taste
Good source of essential vitamins and minerals
Convenient-needs no refrigeration
Gluten-free
Nutrient Profile per 5 oz: Calories 250, Protein 10.9%, Total Fat 34.9%, Carbohydrate 54.2%

Ingredients

Vanilla: -D Nonfat Milk, Water, Sugar (Sucrose), Partially Hydrogenated Soybean Oil, Modified Food Starch, Magnesium Sulfate, Sodium Stearoyl Lactylate, Sodium Phosphate Dibasic, Artificial Flavor, Ascorbic Acid, Zinc Sulfate, Ferrous Sulfate, Alpha-Tocopheryl Acetate, Choline Chloride, Niacinamide, Manganese Sulfate, Calcium Pantothenate, FD&C Yellow #5, Potassium Citrate, Cupric Sulfate, Vitamin A Palmitate, Thiamine Chloride Hydrochloride, Pyridoxine Hydrochloride, Riboflavin, FD&C Yellow #6, Folic Acid, Biotin, Phylloquinone, Vitamin D3 and Cyanocobalamin.

Protein

The protein source is nonfat milk.
Nonfat milk 100%

Fat

The fat source is hydrogenated soybean oil.
Hydrogenated Soybean Oil 100%

Carbohydrate

ENSURE PUDDING contains a combination of sucrose and modified food starch. The mild sweetness and flavor variety (vanilla, chocolate, butterscotch, and tapioca) help prevent flavor fatigue. The product contains 9.2 grams of lactose per serving.

Vanilla and Other Nonchocolate Flavors

| | |
|---|---|
| Sucrose | 56% |
| Lactose | 27% |
| Modified food starch | 17% |

Chocolate

| | |
|---|---|
| Sucrose | 58% |
| Lactose | 26% |
| Modified food starch | 16% |

I. Ensure® with Fiber

Usage: ENSURE WITH FIBER is a fiber-containing, nutritionally complete liquid food designed for people who can benefit from increased dietary fiber and nutrients. ENSURE WITH FIBER is suitable for people who do not require a low-residue diet. It can be fed orally or by tube, and can be used as a nutritional supplement to a regular diet or, in appropriate amounts, as a meal replacement. ENSURE WITH FIBER is lactose- and gluten-free, and is suitable for use in modified diets, including low-cholesterol diets.

Patient Conditions

For patients who can benefit from increased dietary fiber and nutrients

Features

New advanced formula-low in saturated fat, higher in vitamins and minerals
Contains 6 g of total fat and <5 mg of cholesterol per serving Rich, creamy taste Good source of fiber Excellent source of essential vitamins and minerals For low-cholesterol diets Lactose- and gluten-free

Ingredients

Vanilla: -D Water; Maltodextrin (Corn), Sugar (Sucrose), Sodium and Calcium Caseinates, Oat Fiber, High-Oleic Safflower Oil, Canola Oil, Soy Protein Isolate, Corn Oil, Soy Fiber, Calcium Phosphate Tribasic, Magnesium Chloride, Potassium Citrate, Cellulose Gel, Soy Lecithin, Potassium Phosphate Dibasic, Sodium Citrate, Natural and Artificial Flavors, Choline Chloride, Magnesium Phosphate, Ascorbic Acid, Cellulose Gum, Potassium Chloride, Carrageenan, Ferrous Sulfate, Alpha-Tocopheryl Acetate, Zinc Sulfate, Niacinamide, Manganese Sulfate, Calcium Pantothenate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Potassium Iodide, Sodium Selenate, Phylloquinone, Vitamin D3 and Cyanocobalamin.

Protein

The protein source is a blend of two high-biologic-value proteins-casein and soy.

| | |
|---|---|
| Sodium and calcium caseinates | 80% |
| Soy protein isolate | 20% |

Fat

The fat source is a blend of three oils: high-oleic safflower, canola, and corn.

| | |
|---|---|
| High-oleic safflower oil | 40% |
| Canola oil | 40% |
| Corn oil | 20% |

The level of fat in ENSURE WITH FIBER meets American Heart Association (AHA) guidelines. The 6 grams of fat in ENSURE WITH FIBER represent 22% of the total calories, with 2.01% of the fat being from saturated fatty acids and 6.7% from polyunsaturated fatty acids. These values are within the AHA guidelines of ≦30% of total calories from fat, <10% of the calories from saturated fatty acids, and ≦10% of total calories from polyunsaturated fatty acids.

Carbohydrate

ENSURE WITH FIBER contains a combination of maltodextrin and sucrose. The mild sweetness and flavor variety (vanilla, chocolate, and butter pecan), plus VARI-FLAVORS® Flavor Pacs in pecan, cherry, strawberry, lemon, and orange, help to prevent flavor fatigue and aid in patient compliance.

Vanilla and Other Nonchocolate Flavors

| | |
|---|---|
| Maltodextrin | 66% |
| Sucrose | 25% |
| Oat Fiber | 7% |
| Soy Fiber | 2% |

Chocolate

| | |
|---|---|
| Maltodextrin | 55% |
| Sucrose | 36% |
| Oat Fiber | 7% |
| Soy Fiber | 2% |

Fiber

The fiber blend used in ENSURE WITH FIBER consists of oat fiber and soy polysaccharide. This blend results in approximately 4 grams of total dietary fiber per 8-fl. oz can. The ratio of insoluble to soluble fiber is 95:5.

The various nutritional supplements described above and known to others of skill in the art can be substituted and/or supplemented with the PUFAs produced in accordance with the present invention.

J. Oxepa™ Nutritional Product

Oxepa is a low-carbohydrate, calorically dense, enteral nutritional product designed for the dietary management of patients with or at risk for ARDS. It has a unique combination of ingredients, including a patented oil blend containing eicosapentaenoic acid (EPA from fish oil), γ-linolenic acid (GLA from borage oil), and elevated antioxidant levels.

Caloric Distribution

Caloric density is high at 1.5 Cal/mL (355 Cal/8 fl oz), to minimize the volume required to meet energy needs. The distribution of Calories in Oxepa is shown in Table A.

TABLE A

Caloric Distribution of Oxepa

| | per 8 fl oz. | per liter | % of Cal |
|---|---|---|---|
| Calories | 355 | 1,500 | — |
| Fat (g) | 22.2 | 93.7 | 55.2 |
| Carbohydrate (g) | 25 | 105.5 | 28.1 |
| Protein (g) | 14.8 | 62.5 | 16.7 |
| Water (g) | 186 | 785 | — |

Fat

Oxepa contains 22.2 g of fat per 8-fl oz serving (93.7 g/L).

The fat source is an oil blend of 31.8% canola oil, 25% medium-chain triglycerides (MCTs), 20% borage oil, 20% fish oil, and 3.2% soy lecithin.

Oxepa provides a balanced amount of polyunsaturated, monounsaturated, and saturated fatty acids.

Medium-chain triglycerides (MCTs)—25% of the fat blend—aid gastric emptying because they are absorbed by the intestinal tract without emulsification by bile acids.

Carbohydrate

The carbohydrate content is 25.0 g per 8-fl-oz serving (105.5 g/L).

The carbohydrate sources are 45% maltodextrin (a complex carbohydrate) and 55% sucrose (a simple sugar), both of which are readily digested and absorbed.

The high-fat and low-carbohydrate content of Oxepa is designed to minimize carbon dioxide ($CO_2$) production. High $CO_2$ levels can complicate weaning in ventilator-dependent patients. The low level of carbohydrate also may be useful for those patients who have developed stress-induced hyperglycemia.

Oxepa is lactose-free.

Dietary carbohydrate, the amino acids from protein, and the glycerol moiety of fats can be converted to glucose within the body. Throughout this process, the carbohydrate requirements of glucose-dependent tissues (such as the central nervous system and red blood cells) are met. However, a diet free of carbohydrates can lead to ketosis, excessive catabolism of tissue protein, and loss of fluid and electrolytes. These effects can be prevented by daily ingestion of 50 to 100 g of digestible carbohydrate, if caloric intake is adequate. The carbohydrate level in Oxepa is also sufficient to minimize gluconeogenesis, if energy needs are being met.

Protein

Oxepa contains 14.8 g of protein per 8-fl-oz serving (62.5 g/L).

The total calorie/nitrogen ratio (150:1) meets the need of stressed patients.

Oxepa provides enough protein to promote anabolism and the maintenance of lean body mass without precipitating respiratory problems. High protein intakes are a concern in patients with respiratory insufficiency. Although protein has little effect on $CO_2$ production, a high protein diet will increase ventilatory drive.

The protein sources of Oxepa are 86.8% sodium caseinate and 13.2% calcium caseinate.

The amino acid profile of the protein system in Oxepa meets or surpasses the standard for high quality protein set by the National Academy of Sciences.

* Oxepa is gluten-free.

What is claimed is:

1. A composition consisting of at least one monovalent oligosaccharide, wherein said at least one monovalent oligosaccharide binds to Shiga-toxin or Shiga-like toxin.

2. The composition of claim 1 wherein said composition further comprises electrolytes.

3. The composition of claim 1 wherein said at least one monovalent oligosaccharide is selected from the group consisting of globotriose, galabiose, globotetraose and Forssamm antigen.

4. The composition of claim 3 wherein said at least one monovalent oligosaccharide is globotriose.

* * * * *

UNITED STATES PATENT AND TRADEMARK OFFICE
CERTIFICATE OF CORRECTION

PATENT NO. : 6,596,707 B2  Page 1 of 1
DATED : July 22, 2003
INVENTOR(S) : James L. Leach et al.

It is certified that error appears in the above-identified patent and that said Letters Patent is hereby corrected as shown below:

Column 24,
Line 25, add claim 5 as follows: 5. The composition of claim 1 wherein said composition is selected from the group consisting of a pharmaceutical composition and a nutritional composition.

Signed and Sealed this

Thirtieth Day of March, 2004

JON W. DUDAS
*Acting Director of the United States Patent and Trademark Office*